(12) United States Patent
Zadini et al.

(10) Patent No.: US 6,203,527 B1
(45) Date of Patent: Mar. 20, 2001

(54) BI-DIRECTIONAL CLAMPING GUARD FOR NEEDLE STICK PROTECTION

(76) Inventors: Filiberto P. Zadini; Giorgio C. Zadini, both of 2237 Hilltop La., Camarillo, CA (US) 93012

( * ) Notice: Subject to any disclaimer, the term of this patent is extended or adjusted under 35 U.S.C. 154(b) by 0 days.

(21) Appl. No.: 08/593,180

(22) Filed: Feb. 1, 1996

Related U.S. Application Data

(63) Continuation-in-part of application No. 08/219,373, filed on Mar. 29, 1994, now abandoned.

(51) Int. Cl.[7] ................................................. A61M 5/00
(52) U.S. Cl. ................................................ 604/110; 604/198
(58) Field of Search .......................... 604/110, 263, 604/192, 198; 128/919

(56) References Cited

U.S. PATENT DOCUMENTS

| | | | |
|---|---|---|---|
| 5,026,353 | * | 6/1991 | Bartman ............................. 604/192 |
| 5,322,517 | * | 6/1994 | Sircom et al. ..................... 604/263 |
| 5,342,320 | * | 8/1994 | Cameron ........................... 604/192 |
| 5,344,408 | * | 9/1994 | Partika .............................. 604/263 |

\* cited by examiner

Primary Examiner—Anh-Tuan T. Nguyen

(57) ABSTRACT

A needle stick protecting device slideably mounted over medical needles having pointed tips, comprising at least two clamping members sliding over the needle shaft and joined together at their proximal end, automatically arresting in proximity of the needle tip upon passage of triggerng means beyond the needle tip, said triggering means projecting toward the needle from said clamping members. Said clamping of said clamping member on the needle shaft is bi-directional, as it occurring both in response to application of a force for forward sliding of the guard toward the needle tip and in response to a force applied to withdraw said guard from the needle tip. Another relevant feature of the device is the negligible friction opposed by said guard to forward sliding motion, said friction being variable and proportionally dependent to the force applied for forward sliding motion.

11 Claims, 6 Drawing Sheets

BI-DIRECTIONAL CLAMPING GUARD FOR NEEDLE STICK PROTECTION

RELATED CASES

This application is a continuation-in-part of our prior patent application, Ser. No. 08/219,373, filed Mar. 29, 1994 and now abandoned.

FIELD OF THE INVENTION

This invention relates to protective devices for health care workers. More specifically the present invention relates to devices which protect health care workers from accidental punctures due to pointed needles of medical devices.

BACKGROUND-DESCRIPTION OF PRIOR ART

Pointed needles of medical devices, either hollow or solid represent a real hazard to health care workers. Besides causing puncture wounds which carry the risk of infection of skin and deeper structures such as the subcutaneous tissue, the fascia, the muscle and bone, they can transmit multisystem diseases to the health care workers victim of accidental exposure. Numerous are the diseases that have the potential to be transmitted via accidental sticks: hepatitis, malaria, syphilis and, the most frightening of all, AIDS. Risks of transmission are inherent to the medical profession and strict prevention guidelines cannot eliminate the hazards completely. The only successful way to avoid accidental exposure is to provide all the medical devices having pointed needles with protective mechanisms which safely shield the pointed needles from accidental exposures.

A search in the patent office has revealed numerous protective devices for the exposed needle tip of medical devices. Two are the basic mechanisms of protection applied to medical needles.

In one type of devices the needle is retracted and enclosed within a protective shield either manually or by resilient means.

In the other type of devices a protective sleeve or guard is advanced manually or by resilient means over the needle enclosing the needle as a whole or enclosing just the pointed tip. Various are the mechanisms described for achieving the locking of the sleeve or guard in respect to the needle and various are the needle tip shielding mechanisms in either group of devices.

While our search revealed many protecting mechanisms in which the needle guard is a part of the housing of the medical device to which the needle is applied to, or is simply connected to, we found only two patents, U.S. Pat. No. 4,929,241 issued to John Kully and Patent Cooperation Treaty application No. PCT/CA 90/00031, published on Aug. 9, 1990 under International Publication No. WO 90/08564 issued to Inventor Robert Sircom, in which the protecting mechanism is a separated unit, i.e. with no attachment of any sort, from the medical device to which the needle is applied. In U.S. Pat. No. 4,929,241 issued to Kully, a medical needle puncture guard is described in which a small protective guard slides over a medical needle. The front portion of the device comprises two jaws which collapse in front of the needle tip, once the needle tip is passed, to form a barrier in front of the needle tip. Arrest of the jaws in front of the needle tip is accomplished by two distinct mechanisms: anterograde arrest is accomplished by two opposing sharp blades projecting inward toward the needle shaft from the jaws, both obliquely and anteriorly oriented, exerting pressure on the needle shaft to the point of arresting its forward sliding motion impeding further advancement, once the transverse shields of the jaws have passed the needle tip.

Retrograde arrest is accomplished by the transverse barrier resulting from the collapsing of the transverse shields, as shown in FIG. 1, of the above cited U.S. Pat. No. 4,929,241 of the opposing jaws in front of the needle tip. The two jaws which collapse in front of the needle tip are each secured to mounting means. Collapse of the opposing jaws in front of the needle tip and arrest of the guard to forward motion by the opposing blades exerting arrest pressure over the needle shaft is necessarily accomplished by the resiliency of the jaws, said jaws urging opposed transverse shields 24 and 26 and opposed arresting blades to close on the needle shaft.

An unavoidable consequence of such concept is that the arrest to forward motion of the needle guard relies exclusively upon the degree of the pressure exerted by the opposing arresting blades upon the needle shaft, such degree of pressure on the needle shaft being dependent upon the degree of resiliency of the jaws to which said blades are secured. If such degree of resiliency is insufficient, then the needle guard will not arrest in proximity of the needle tip and the needle guard will inevitable fall off the needle defeating the purpose of the device, unless of course, modifications to the surface of the needles currently in the market are made, as for instance an arresting step, modifications which besides not being disclosed in such patent publication, do not appear to be reasonably practical.

The requirement for a resiliency of a sufficient degree to enable arrest to forward motion by the opposing arrest blades exerting pressure upon the needle shaft results in the drawback, inherent to the concept of the art disclosed by Kully, that also the transverse shields will inevitably be subjected to the same degree of resiliency which urges the opposing arresting blades to close together on the needle shaft because, alike arresting blades, transverse shields are secured to the same resilient jaws. As a result of the significant resiliency which transverse shields are subjected to while sliding forward along the needle shaft, the dynamic resistance and friction of the guard to forward sliding motion is also significant. In certain applications, such degree of friction is undesirable and in others it limits the usefulness of the device. More important than that, it appears that the needle guard disclosed by Kully does not guarantee an arrest to forward sliding motion of the guard, in fact, if the operator of the device advances the guard rapidly and forcefully, the guard may exit from the tip of the needle without arresting in proximity of the needle tip, unless the centripetal forces of the blades on the needle shaft is so impractically relevant to interfere with smooth and unopposed sliding of the guard over the needle. As a matter of fact, the arrest of the guard in the cited patent by Kully occurs as a probable event dependent upon the degree of centripetal force continuously exerted by the opposing blades during the slide motion of the guard on the needle shaft by resilient jaws.

Patent Cooperation Treaty application No. PCT/CA 90/00031, published on Aug. 9, 1990 under International Publication No. WO 90/08564 issued to Inventor Robert Sircom discloses a needle guard in which arrest to forward motion of the needle guard is accomplished by a locking plate having an orthogonally formed passageway for the needle shaft, said plate being orthogonally angled in respect to the longitudinal axis of the needle when being advanced along the needle, said orthogonally angled position being maintained by a sensing plate connected to the locking plate through an arm named canting lever. Contact of the sensing plate on the needle shaft is maintained by a spring arranged to secure such contact. Upon passage of the needle tip, the arm named canting lever, no longer retained in its position by the sensing plate sliding over the needle shaft, is driven further toward the needle by the spring causing canting of the locking plate in respect to the needle shaft. Said canting of the locking plate causes arrest of the plate by gripping exerted on the needle shaft by the sharp edges of the passageway formed in the locking plate in two points along the needle shaft in proximity of the tip opposite although not equidistant from the needle tip.

The locking mechanism of gripping type disclosed above provides a type of arrest of the needle guard on the needle shaft in proximity of the tip only in response to forward sliding motion of the guard over the needle. Backward sliding motion of the needle guard, i.e. withdrawal of the needle guard along the needle and exposure of the needle tip, is prevented, as in the case of Kully's patent, by the presence of a front plate, named sensing plate, collapsed just in front of the needle tip as in the Kully patent.

The presence of the spring disclosed by Sircom constitutes a significant drawback due to the friction caused by said spring urging the sensing plate against the needle shaft. As in the case of Kully's patent, such friction is constant regardless of the degree of force applied for forward sliding motion of the guard on the needle. Faster forward sliding motion will not increase the contact force and friction upon the needle shaft by the sensing means in either patent with resulting diminished reliability of the device in timely responding with self-arrest in proximity of the needle tip.

Our patent search has revealed that no known patent describes the mechanism of needle stick protection that we describe here in the present application.

BRIEF SUMMARY AND OBJECTIVES OF THE INVENTION

It is an objective of our invention to provide medical needles, either solid or hollow, with a simple, safe, effective mechanism of shielding.

Is is another object of our invention to provide medical needles with a type of protective mechanism capable of performing equally in needles of various type regardless of size, length, shape or structure of the needle.

It is an object of our invention to provide the operator with a compact easily to assemble and easy to operate needle stick protector.

Our invention describes a needle protective mechanism consisting of a protecting guard slideable over a medical needle, said needle guard being capable of self arrest and irreversible locking once the needle tip is passed beyond the front portion of the device, shielding so irreversibly the needle tip from accidental exposures. The locking mechanisms are automatically actuated once the device reaches the tip of the medical needle.

Both anterograde and retrograde sliding motion of the guard over the needle is accomplished by a clamping action upon the needle shaft. Attempts to dislodge the guard from the tip of the needle by a forwardly directed sliding force as well as by a backwardly directed sliding force will result in a further increase of said clamping action on the needle shaft. Therefore the higher the degree of force applied to dislodge the guard from the needle tip, the more firmly the needle guard will clamp to the needle tip, rendering attempts of dislodging the guard virtually impossible and the needle tip protection very reliable, as it should be.

Our application describes a device composed of a housing generally of cylindrical shape in which clamping members are enclosed. The triggering of the arrest and locking of the clamping members over the needle upon sliding of a portion of the device along the needle tip is achieved automatically, and is actuated by one or two triggering means.

In our application, the arrest occurs inevitably and irreversibly as a result of application of external forces specifically applied by the operator upon the housing of the device, said forces being exerted by the operator in parallel direction to the needle shaft. Such forces, parallel to the longitudinal axis of the needle, will suddenly change direction from parallel to centripetal toward the needle once the front portion of the device is advanced beyond the needle tip, causing an irreversible arrest and locking of the device on the needle.

Furthermore increasing the force driving the guard beyond the needle tip will further strengthen the arrest and locking mechanism, the opposite in respect of the patents cited in which pushing further and stronger will increase the probability of exit of the guard beyond the needle tip with resulting failure.

DETAILED DESCRIPTION OF THE INVENTION

Figure 1:
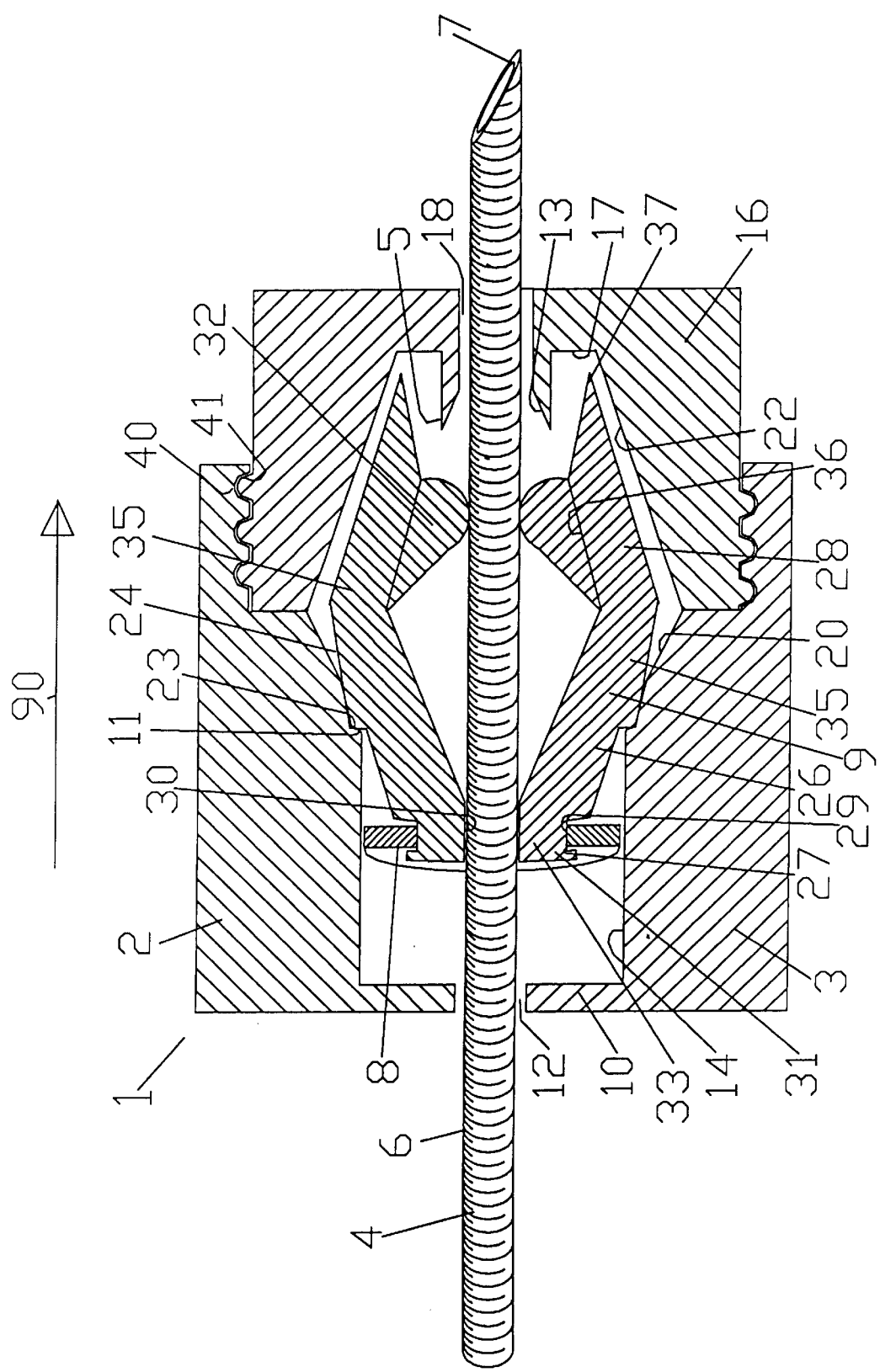
FIG. 1 is a longitudinal cross section of the device mounted over the medical needle in position of rest with the clamping mechanisms prior to actuation.

In that form of the present invention chosen for the purpose of illustration in FIG. 1 a needle stick protecting device generally indicated at 1, is shown comprising housing means 2 generally of hollow cylindrical shape concentric to and slideable over a medical needle 4 and clamping members 35 encircling needle 4. Housing means 2 is composed of body 3 and of a front portion 16 assembled together via mating thread 40 and 41. Body 3 of housing means 2 has base 10, with at its center opening 12 for passage of medical needle 4, cylindrical side walls 14, generally parallel to needle shaft 6, and slanted wall 20, starting at housing interface means or flange 11 for engagement with corresponding flange or clamping interface means 23 of clamping member 35 as it will be described below. Front portion 16 of housing means 2, with at its center passageway 18 for needle 4, has slanted wall 22 and circular latches 5 or latch means or locking means backwardly projecting from anterior wall 17 of said front portion 16. Said latches 5 have a slanted surface 13 for engagement to tip 37 of clamping members 35 as it will be described below.

Needle 4 is composed of a shaft 6 and a tip 7.

Clamping means 9 is composed of two symmetrically opposed identical clamping members 35 at opposite site of needle shaft 6. Each clamping member 35 of clamping means 9 is composed of proximal or posterior arm 26 and of anterior or distal arm 28 connected at obtuse angle in respect of each other. Each posterior arm 26 of clamping member 35 has, proximally, a posterior segment 33 with posterior end 31 and with clamping surface 30 for engagement with needle shaft 6, a semiannular indentation or groove 29 for O ring 8, and has flange 23 on its outer surface 24 for engagement to corresponding interface means 11 of body 3 of housing 2. Such flange 23 projects from proximal arm 26 at suitable angle from said proximal arm to convert the majority of the force applied by interface means 11 into forward sliding motion and a small fraction of said force into a force inducing contact of triggering means 32 upon needle shaft 6, as it will described below.

Anterior or distal arm 28 of clamping members 35 has a portion of its length 32 in slideable contact with needle shaft 6, said portion being adapted as triggering means 32 of mammillary shape or triggering means or mammilary bodies, projecting from inner surface 36 of clamping members 35 and tip 37 for wedged engagement with latches 5.

With the device in a position of rest, triggering members 32 are in sliding contact with needle shaft 6.

Description of Operations

Figure 2:
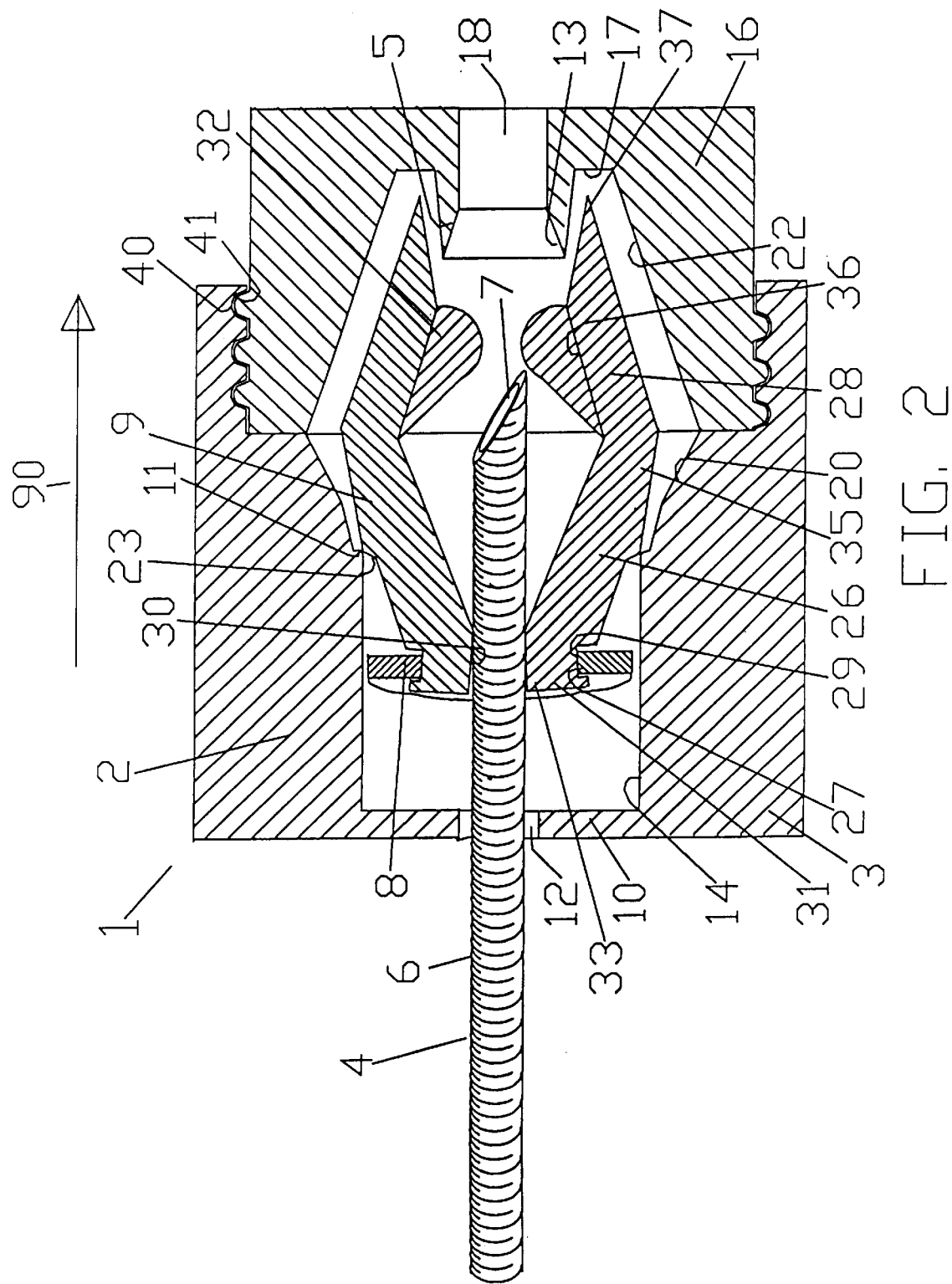
FIG. 2 is a view of the device of FIG. 1 shown in an advanced position in respect to the needle with the clamping mechanisms at an early stage of actuation.

In FIG. 2, the needle guard 1 is shown while being slided forwardly. Needle guard 1 may be either advanced manually by the operator or by resilient means. Advancement is extremely smooth and requires minimal thrust as friction is negligible as housing means 2 forwardly thrusted by the operator is acting upon the very proximal segment of each proximal arm 26 of clamping members 35 via interface means 11. In fact, as housing means 2 exerts its force via interface means 11 acting upon flange 23 on the very proximal segment of proximal arm 26 of clamping members 35, the centripetal component of the forward thrusting force is greatly reduced to almost a negligible factor.

The described system is the equivalent of a lever system in which the acting force is applied close to the fulcrum of a lever. In FIG. 2 the lever is represented by proximal arm 26 of clamping members 35, the fulcrum is represented by the proximal end 31 of proximal arm 26 and the point of applied force is the flange 23.

Friction of triggering means on needle shaft is even further lightened by the angle of flange 23 on proximal arm 26 of clamping member 35, said angle resulting in a surface of suitable inclination being opposed to the corresponding interface means 11 of housing 2 to convert the majority of the force applied by interface means 11 into forward sliding motion and only a small fraction of said force into a force inducing friction by sliding contact of said triggering means 32 upon needle shaft 6.

Triggering means or members 32 of clamping members 35 will exert only a negligible force resulting in a negligible friction over needle shaft 6 during the advancement by sliding motion of device 1 over needle 4. Remarkably, no additional active forces, in particular no resilient means need to assist triggering means 32 in maintaining their sliding contact with needle shaft 6. In Applicants invention, the force resulting into friction will only increase when a fast sliding motion of the guard along the needle shaft is exerted upon the guard: such a correlation of contact force of triggering means 32 upon needle shaft 6 with the applied force for forward sliding motion is an appropriate and a desired correlation which enhances the reliability of the device in clamping rapidly in response to triggering, adapting to different forward sliding speeds.

Upon passage of the triggering means 32 beyond needle tip 7, triggering means 32, no longer maintained far apart or open by the presence of the needle shaft, will be permitted to close, i.e. to slightly converge one toward the other by the slight force applied to flange 23 of clamping members 35 by interface means 11. The slight converging of the triggering means will result in tilting of the clamping members 35 from which the triggering means 32 are projecting. As shown in FIG. 2, such tilting of clamping members 35 will allow disengagement of the flange 23 from interface means 11. As a result of such disengagement, as shown in FIG. 3, interface means 11 will act upon outer surface of clamping members 35 causing conversion of the whole applied force into a force resulting into a clamping of said clamping members 35 upon said needle 4 via clamping surface 30.

Figure 3:
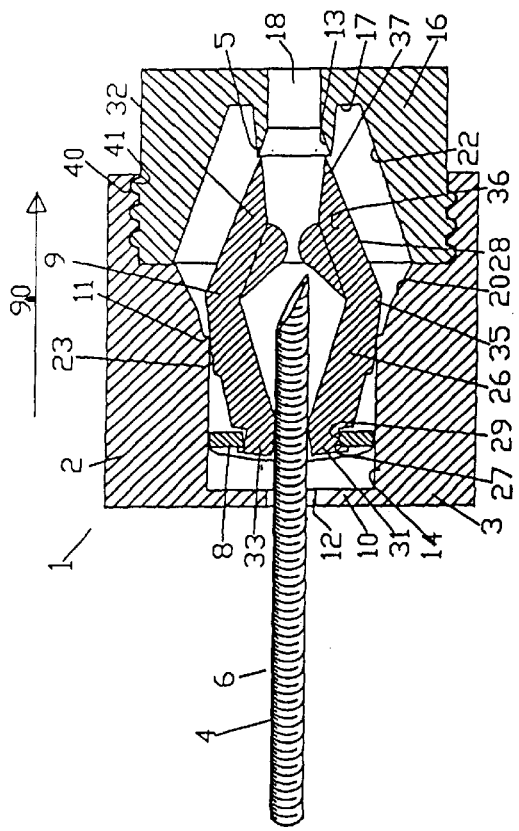
FIG. 3 is a view of the device of FIG. 1 with the clamping mechanisms in a further stage of actuation.
Figure 4:
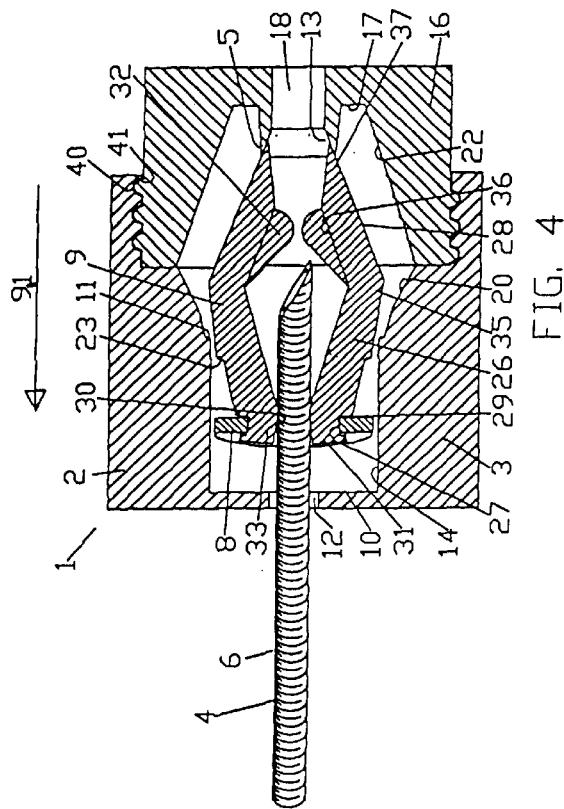
FIG. 4 is a view of the device of FIG. 1 with the clamping mechanisms fully actuated.

Tip 37 of clamping members 35, as shown in FIG. 3, are shown in an early stage of wedging engagement with circular latches 5 of front portion 16 of housing 2. In FIG. 4 such wedging engagement of tip 37 of clamping members 35 is completed and any attempt to backwardly dislodge the guard from the needle tip will result into a further strengthening of the clamping action of clamping members 35 upon needle shaft 6. Such wedged engagement of tip 37 of clamping members 35 with latches 5 will result, therefore, in an irreversible locking of the needle guard over the needle tip, effectively shielding so the needle tip from accidental exposures, not allowing the exit of needle tip 7 from passageway 18 of housing 2. FIG. 2 illustrates tips 37 at the beginning of their movement away from latch 5, while FIG. 3 illustrates tips 37 at the end of such movement. When moving distally to latch 5, tips 37 gradually approximate to each other as a result of the action of flange or interface means 11 of housing means 2 upon outer surface 24 of proximal arm 26 of clamping members 35. In fact, body 3 of housing means 2 is moved relatively to needle 4 in direction of arrow 90 represented above device 1, moved either by the hands of the operator of the device or by a resilient means. As a consequence of that movement of body 3 of housing means 2, flange 11, which belongs to body 3 of housing 2, will also move relatively to needle 4 in direction of arrow 90. As represented in FIG. 3, flange 11 has also moved in direction of arrow 90 relatively to clamping members 35 which conversely, by clamping upon needle 4 with their surface 30, will not be allowed to move relatively to needle 4.

Once tips 37 of clamping members 35 are fully approximated to each other as shown in FIG. 3, tips 37 will not be allowed to open or diverge from their fully approximated position when moving proximally to latch 5 for the reason described below.

When housing means 2 are moved in the direction represented by arrow 91 above device 1 of FIG. 4, latch 5, which belongs to housing means 2, will move proximally to tips 37, i.e. tips 37 move proximally to latch 5. When tips 37 move proximally to latch 5, clamping members 35, and therefore their tips 37, will remain in their reciprocal position, i.e. they will not be allowed to diverge, because, as shown in FIG. 4, O-ring 8, which seats in groove 29 of clamping members 35, will be forced to slide distally within groove 29, toward the tip of the needle, as best shown in FIG. 4, due to radial expansion of posterior segments 27 of groove 29 resulting from the posterior diverging of posterior segments 33 of proximal arms 26 of clamping members 35, said diverging resulting in turn from the tilting of clamping members 35 produced when housing means 2 are moved in direction of arrow 90 represented above device 1 of FIG. 3, after clamping members 35 have reached needle tip 7. Radial expansion of posterior segment 27 of groove 29 occurring when clamping members 35 are being closed, necessarily results, as shown in FIGS. 3 and 4, in some constriction of the needle shaft, because, in a stage when clamping members 35 are sliding along the needle, clamping surface 30, which, as shown in FIG. 1 is generally flat and parallel to needle shaft 6, is kept in close contact with the needle by O-ring 8, again as shown in FIG. 1. Said radially expanded posterior segment 27 of groove 29 prevents O-ring 8 from being displaced backward within groove 29 because said expanded posterior segment of groove 29 would no longer fit within O-ring 8 internal diameter. As a result of that, clamping members 35 will remain closed, and their tips 37 will remain approximated even after flange 11 is removed from clamping members 35. Therefore, when moving proximally to latch 5, tips 37 will have no other alternative than following the path of entering inside latch 5.

Figure 5:
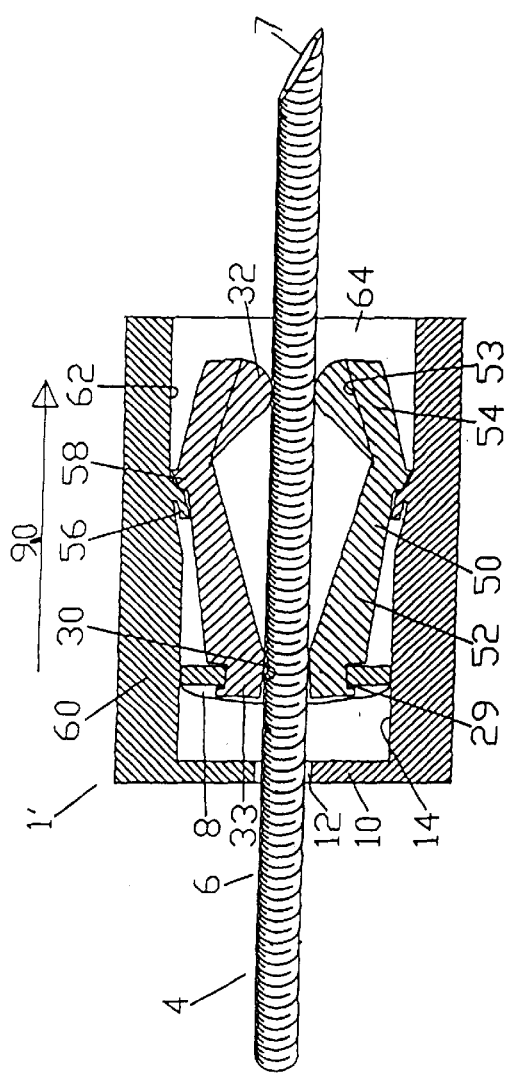
FIG. 5 is a view of an alternative version of the device of FIG. 1 in a stage prior to actuation of the clamping mechanism.
Figure 6:
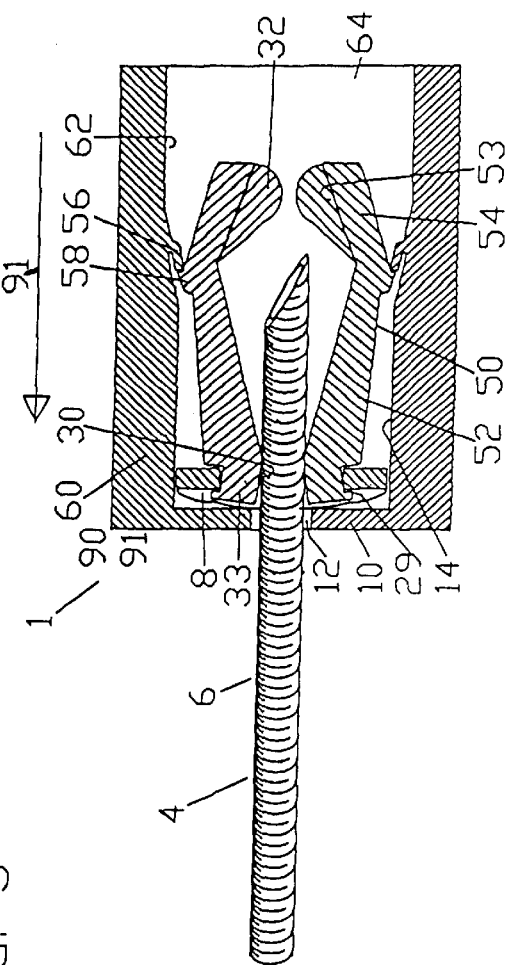
FIG. 6 is a view of the device of FIG. 5 with the clamping mechanism fully actuated.

FIGS. 5 and 6 show an alternative form of the device of FIGS. 1 to 4. Said alternative form 1' of the device is essentially identical to device 1 of FIGS. 1 to 4, except for the type of interface means or latch 56 or latch means or locking means of housing 60 on side wall 14 of housing means 60 and for corresponding interface means or latch 58 or latch means or locking means of clamping members 50. Indeed in this version of the device, a single structure has the dual function of interface means and locking means. Clamping members 50 are composed of proximal or posterior arm 52 and of distal or anterior arm 54 connected at obtuse angle in respect of each other. Triggering means 32 are projecting from inner surface 53 of distal arm 54 of clamping member 50. Housing means 60 has anterior segment 62 with opening 64 for passage of needle 6. In such alternative form, latch 58 is formed in the outer surface of the clamping members 50.

Description of Operation

In use, the device is operated as the device of FIGS. 1 to 4, however, engagement of interface means 56 with flange 58 in this alternative form prevents release of the clamping of the clamping members 50.

Figure 7:
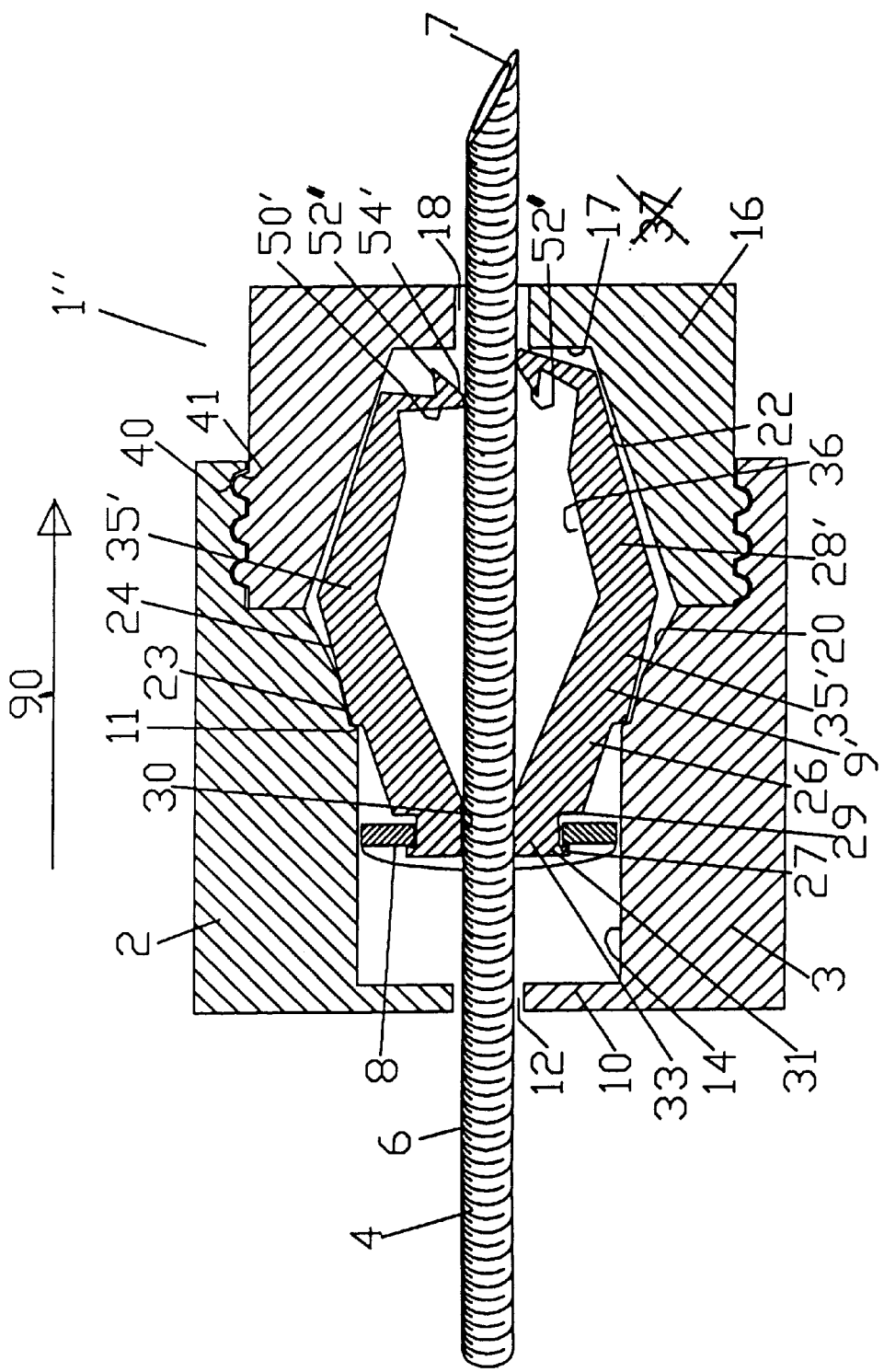
FIG. 7 is a view of an alternative version of the device of FIG. 1 in a stage prior to actuation of the clamping mechanism.
Figure 8:
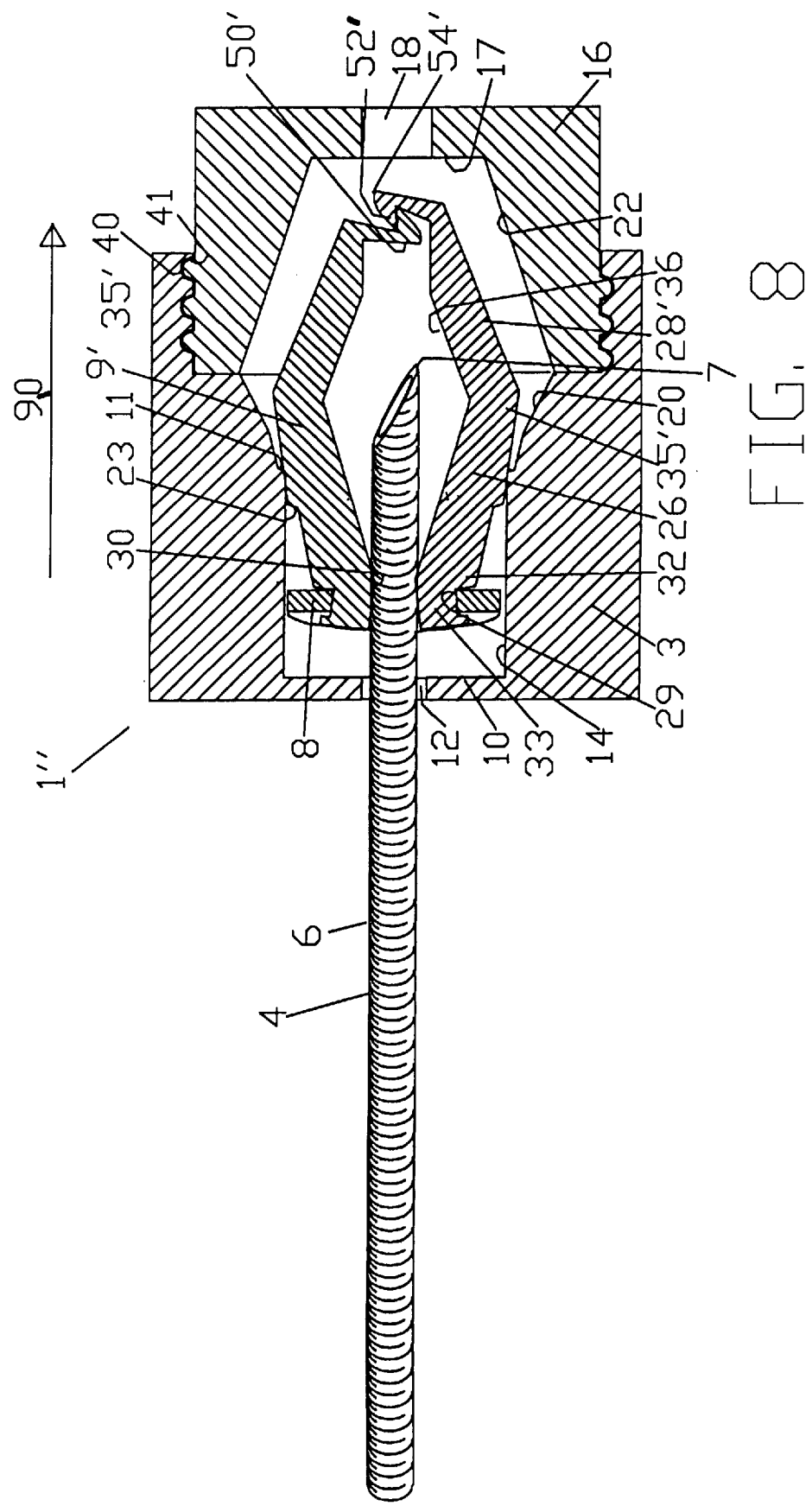
FIG. 8 is a view of the device of FIG. 7 with the clamping mechanism fully actuated.

FIGS. 7 and 8 show an alternative form of device 1 of FIGS. 1 to 4. This alternative form 1" of the device is similar to device 1 of FIGS. 1 to 4 except for a few differences which are outlined below.

Anterior or distal arms 28' of clamping members 35' of clamping means 9' have distal segments 50' projecting inwardly at an angle from anterior or distal arms 28'. Distal segments 50' are formed with resilient interlocking latches or hooks or means 52' and triggering means 54'. Mammillary bodies 32 are no longer present in anterior arms 28 of clamping members 35. Distal segments 50' of anterior arms 28' are with the device in position of rest in slideable contact with needle shaft 6 via triggering means 54'. Front portion 16 of housing means 2 is no longer formed with circular latches 5.

Description of Operation

The device 1" is operated as device 1 of FIGS. 1 to 4. Needle guard 1" is slided along needle shaft 6 of needle 4 from a position distal to tip 7 toward tip 7 either manually by the operator or by resilient means. During the advancement by sliding motion of device 1" over needle 4, triggering means 54' of clamping member 35' will exert only a negligible pressure upon needle shaft 6, resulting in a negligible friction on needle shaft 6. The operational steps for device 1" are the same as for device 1 of FIGS. 1 to 4. Upon passage of triggering means 54' beyond needle tip 7, clamping members 35', no longer maintained open by triggering means 54' in slideable contact, and at opposite sites, of needle shaft 6, will be permitted to close.

Closing of clamping members 35' upon needle shaft 6 will result with clamping action on needle shaft 6 through clamping surface 29 of clamping members 35'. The clamping action of clamping members 35' will not only prevent exiting of the needle guard from the needle by preventing further sliding of the clamping members in the direction the needle guard was being moved, but it will also prevent sliding in the opposite direction of the clamping members.

Upon closure of clamping members 35', hooks 52' will reciprocally by first coming to reciprocal sliding contact and reciprocally displacing each other as a result of said sliding contact, then returning to resting position as a result of their resiliency when clamping members 35' are fully closed. The return to resting position of hooks 52' upon closure of clamping members 35' will result with an irreversible interlocking of clamping members 35' in closed position.

The irreversible interlocking of clamping members 35' in closed position thereforel results in a bidirectional self-arrest of needle guard 1" on the needle, i.e.the needle guard will be automatically prevented from sliding in either direction along the needle and will provided an effective needle shield for accidental needle stick injury.

What we claim is:

1. A needle guard for prevention of accidental punctures, said guard being slideably mounted adjacent a hypodermic needle having a shaft and a tip, said guard comprising:

clamping means slideably mounted on the needle, and having at least two clamping members, said clamping members being arranged so as to at least partially oppositely face each other about a longitudinal axis of the needle shaft, said clamping members being proximally pivotably joined, having at least one portion adapted for slideable contact with the needle shaft and having at least one clamping surface for clamping upon the needle, housing means to enclose said clamping means, interface means, between said housing means and said clamping means, for engaging said housing means to said clamping means so as to allow sliding motion of said clamping means along the needle shaft toward the needle tip upon forward motion exerted on said housing means, said interface means comprising a flange means for engaging with said clamping members to force said clamping members closed upon passage beyond the needle tip of said portion of the clamping members adapted for slideable contact with the needle shaft, whereby said housing means and said clamping means permanently shield the needle tip from further exposure or punctures.

2. The needle guard of claim 1, further comprising locking means for unreleasably locking said clamping members closed on the needle shaft by said flange means.

3. The needle guard of claim 2, wherein said locking means comprises:

a latch means formed in a front portion of said housing means unreleasably engaging with a front tip of said clamping members to maintain said clamping members closed on the needle shaft by a reciprocal wedging upon application of a backward sliding force upon said housing means.

4. The needle guard of claim 2, wherein said locking means comprises:

latch means unreleasably engaging said clamping members to said housing means upon a relative advancement of said housing means with respect to said clamping members, said relative advancement of said housing means with respect to said clamping members resulting from said forward motion exerted on said housing means upon an arrest of the forward motion of said clamping members closed on the needle shaft by said flange means upon said passage beyond the needle tip of said portion of the clamping members adapted for slideable contact with the needle shaft.

5. The needle guard of claim 2, wherein said locking means comprises:

hook means unreleasably interlocking said clamping members to each other in a closed position upon a relative advancement of said housing means with respect to said clamping members, said relative advancement of said housing means with respect to said clamping members resulting from said forward motion exerted on said housing means upon an arrest of the forward motion of said clamping members close on the needle shaft by said flange means upon said passage beyond the needle tip of said portion of the clamping members adapted for slideable contact with the needle shaft.

6. The needle guard of claim 1, wherein:

said sliding motion of said clamping members along said needle toward the tip of the needle occurring with a substantially negligible friction resulting from a sliding contact over the needle shaft of said portion of clamping members adapted for slideable contact with the needle, said friction being predominatly dependent upon a force applied for said forward sliding motion of said housing means.

7. The needle guard of claim 1, wherein:

said sliding motion of said clamping members along said needle toward the tip of the needle occuring with a substantially negligible friction resulting from a sliding contact over the needle shaft of said portion of clamping members adapted for slideable contact with the needle, said friction being predominately dependent upon a force applied for said forward sliding motion of said housing means.

8. The needle guard of claim 1, further comprising:

means converting a force applied to said housing means in direction of a proximal end of said needle into a further clamping action upon the needle shaft by said clamping members so that any increase of said force directed toward said proximal end of said needle increases said clamping action.

9. The needle guard of claim 1, wherein:

said flange means force said clamping members closed upon passage beyond the needle tip of said portion of the clamping members adapted for slideable contact with the needle shaft as a result of a tilting of said clamping members occuring upon passage of the tip of the needle beyond said portion of said clamping members in sliding contact with the needle.

10. The needle guard of claim 1, wherein:

a lever mechanism acts to urge said clamping members into engagement with the needle shaft.

11. The needle guard of claim 1, wherein:

said closed clamping members cause a constriction on the needle shaft, so as to further prevent sliding of said clamping members along the needle in either direction.

\* \* \* \* \*